United States Patent [19]

Thorogood

[11] Patent Number: 4,528,195

[45] Date of Patent: Jul. 9, 1985

[54] IMIDAZOLE DERIVATIVES AND SALTS THEREOF, THEIR SYNTHESIS AND INTERMEDIATES AND PHARMACEUTICAL FORMULATIONS

[76] Inventor: Peter B. Thorogood, 114 Venner Rd., Sydenham, London, SE. 26, England

[21] Appl. No.: 250,481

[22] Filed: Apr. 2, 1981

Related U.S. Application Data

[60] Division of Ser. No. 67,109, Aug. 17, 1979, abandoned, which is a continuation-in-part of Ser. No. 8,101, Jan. 31, 1979, abandoned, Ser. No. 952,796, Oct. 19, 1978, abandoned, and Ser. No. 952,774, Oct. 19, 1978, abandoned, said Ser. No. 952,796, is a continuation-in-part of Ser. No. 936,407, Aug. 24, 1978, abandoned, said Ser. No. 952,774, is a continuation-in-part of Ser. No. 936,406, Aug. 24, 1978, Pat. No. 4,284,641.

[30] Foreign Application Priority Data

Feb. 1, 1978 [GB] United Kingdom ............... 03984/78

[51] Int. Cl.³ ................. A61K 31/415; A61K 31/455; A61K 31/44; A61K 27/00
[52] U.S. Cl. .................................... 514/396; 514/398; 514/397; 514/399; 514/365; 514/374
[58] Field of Search ............... 424/273 R, 263, 273 B, 424/267, 248.52, 248.53, 248.5

[56] References Cited

U.S. PATENT DOCUMENTS

| | | | |
|---|---|---|---|
| 3,592,826 | 7/1971 | Marcus | 548/335 |
| 4,006,423 | 2/1977 | Strehlke | 548/335 |
| 4,036,975 | 7/1977 | Walker | |
| 4,118,461 | 10/1978 | Miller | 424/273 R |
| 4,150,153 | 4/1979 | Walker | 424/273 R |
| 4,284,641 | 8/1981 | Thorogood | 424/273 R X |

FOREIGN PATENT DOCUMENTS

| | | | |
|---|---|---|---|
| 46-24143 | 7/1971 | Japan | 548/335 |
| 1122717 | 5/1967 | United Kingdom | |
| 1364312 | 8/1974 | United Kingdom | |

OTHER PUBLICATIONS

Leusen, Chem. Abs., vol. 86, 1977, Ab. No. 189795c.
Schubert, Chem. Abs., vol. 60, 1964, Ab. No. 14494h.
Jones, Canad. J. Chem., vol. 49, 1971, pp. 325–332.
Leusen, J. Org. Chem., vol. 42, 1977, pp. 1153–1159.
Schubert, Wissenschaftliche. Zeit. X1/5, 1962, pp. 603–611.
Ito, Tetrahedron Letters, vol. 18, 1938, pp. 1535–1538.
Tai, Biochem. Biophys. Res. Comm., vol. 80, 1976, pp. 2753–2764.

*Primary Examiner*—Frederick E. Waddell
*Attorney, Agent, or Firm*—Donald Brown

[57] ABSTRACT

Pharmaceutical formulations comprising an imidazole (or pharmaceutically acceptable salt thereof) of formula:

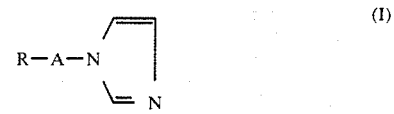

wherein (i) A is an aliphatic hydrocarbon residue of from 1 to 4 carbon atoms and R is a naphthyl, tetrahydronaphthyl, heterocyclyl, arylthio, arylalkylthio, aryloxy, arylalkyloxy, arylhydroxymethylene, arylcarbonyl, arylalkylcarbonyl, alkyloxy, alkylthio or a substituted cycloalkyl or cycloalkenyl group or (ii) A is an —$SO_2$— group and R is aryl or heterocyclyl or (iii) A is a chemical bond and R is a heterocyclyl or Some of these imidazoles and salts are novel.

Methods of preparing the imidazoles are disclosed. The imidazoles and their salts are useful in the treatment or prophylaxis of thrombo-embolic conditions, shock and angina pectoris.

17 Claims, No Drawings

IMIDAZOLE DERIVATIVES AND SALTS THEREOF, THEIR SYNTHESIS AND INTERMEDIATES AND PHARMACEUTICAL FORMULATIONS

CROSS REFERENCE TO EARLIER APPLICATIONS

This application is a division of U.S. patent application Ser. No. 067,109 filed Aug. 17, 1979, now abandoned. Ser. No. 067,109 is a continuation-in-part of (1) U.S. patent application Ser. No. 952,796 filed Oct. 19, 1978, now abandoned which is in turn a continuation-in-part of U.S. patent application Ser. No. 936,407 filed Aug. 24, 1978, now abandoned;

(11) U.S. patent application Ser. No. 952,774 filed Oct. 19, 1978, now abandoned which is in turn a continuation-in-part of U.S. patent application Ser. No. 936,406 filed Aug. 24, 1978, now U.S. Pat. No. 4,284,641 and;

(111) U.S. patent application Ser. No. 8,101 filed Jan. 31, 1979, now abandoned.

The present invention relates to imidazole derivatives and salts thereof, to their synthesis and intermediates therefor; to pharmaceutical formulations containing such compounds and to the use of these compounds in medicine.

Thromboxane $A_2$ ($TXA_2$), a potent stimulator of blood platelet aggregation, is produced in platelets, from the prostaglandin endoperoxides $PGG_2$ and $PGH_2$. Prostacyclin ($PGI_2$), which has potent anti-aggregatory activity, is also produced (in blood vessel walls) from $PGG_2$ and $PGH_2$ and it has been suggested that a balance between the production of $TXA_2$ and $PGI_2$ is the controlling factor in thrombus formation. It would, in consequence, be desirable in the treatment or prophylaxis of thromboembolic disorders to be able to selectively inhibit $TXA_2$ synthetase, thereby favouring the production of the antiaggregatory agent $PGI_2$.

Imidazole and 1-methylimidazole are known to provide some degree of inhibition of the enzymic conversion of the endoperoxides ($PGG_2$ and $PGH_2$) to thromboxane $A_2$ by platelet microsomes (Moncada et al., Prostaglandins, 13/4, 611–618, 1977). Certain 1-n-alkylimidazoles, especially 1-n-dodecylimidazole and its higher homologues have been described as being capable of lowering serum cholesterol levels (U.K. Pat. No. 1 364 312; Biochem. Pharmacol., 24, 1902–1903, 1975).

We have now discovered that $TXA_2$ synthetase may be inhibited by 1-substituted imidazoles of formula (A), and acid addition salts thereof. The compounds of formula (A), especially those of formulae (IA) and (I), and their salts are hereinafter referred to as the "active compounds".

Compounds of formula (A) are:

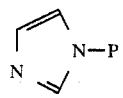

(A)

wherein P is substituted alkyl, substituted cycloalkyl, substituted alkenyl, substituted cycloalkenyl, substituted alkynyl, substituted aryl, substituted arylalkyl, alkylsulphonyl, arylsulphonyl or heterocyclyl; the term "substituted" not here including hydrocarbon substituents.

As used in this specification the term "alkyl" (unless otherwise stated) refers to both straight and branched chain alkyl groups having from 1 to 9 carbon atoms and thus includes primary, secondary and tertiary alkyl groups. Typical alkyl groups include, for example, n-propyl, iso-propyl, n-butyl, iso-butyl, n-pentyl, and n-hexyl.

The term "cycloalkyl" refers to saturated cyclic aliphatic hydrocarbon groups having from 3 to 9 especially 3 to 8, or 4 to 9, carbon atoms such as, for example, cyclopropyl, cyclopentyl and cyclohexyl.

The term "alkenyl" refers to an unsaturated aliphatic hydrocarbon group having from 2 to 9 carbon atoms and one or more carbon-carbon double bonds. Typical alkenyl groups include, for example, 2-propenyl, 2-butenyl and 3-butenyl.

The term "cycloalkenyl" refers to an unsaturated cyclic aliphatic hydrocarbon group having from 3 to 9, especially 3 to 8 or 4 to 9, carbon atoms and one or more carbon-carbon double bonds. Typical cycloalkenyl groups include, for example, cyclopropenyl, cyclopentenyl, cyclohexenyl and 1,4-cyclohexadienyl.

The term "alkynyl" refers to an unsaturated aliphatic hydrocarbon group having from 2 to 9 carbon atoms and one or more carbon-carbon triple bonds. Typical alkynyl groups include 2-propynyl, 2-butynyl and 3-butynyl.

The term "aryl" refers to an aromatic hydrocarbon group, for example phenyl or naphthyl.

The term "arylalkyl" refers to an aryl-substituted alkyl group such as benzyl, phenethyl or phenpropyl.

The term "alkylsulphonyl" refers to a group $-SO_2Alk$ where Alk is alkyl as defined above.

The term "arylsulphonyl" refers to a group $-SO_2Ar$ where Ar is aryl as defined above.

The term "heterocyclyl" refers to a carbocyclic ring, either aromatic or non-aromatic, where one or more carbon atoms have been replaced by heteroatoms, preferably by one or more oxygen, sulphur or nitrogen atoms or $>N-R^5$ groups where $R^5$ is hydrogen or alkyl as defined above. Typical heterocyclyl groups are, for example, tetrahydrofuranyl, tetrahydropyranyl, piperdinyl, 2,5-dihydrofuranyl, furanyl, pyranyl, pyridyl, thienyl, imidazolyl, pyrollyl, pyrollidinyl, pyrimidyl, oxazolyl, and oxathiazolyl.

The group P in formula (A) may optionally be substituted where appropriate with, for example, one or more of alkyl, cycloalkyl, alkenyl, cycloalkenyl, alkynyl, aryl, arylalkyl, hydroxy, alkyloxy, aryloxy, acyl, aroyl, thiol, thioalkyl, arylthio, amino, nitro, halo, cyano, thiocyanato, isothiocyanato, trifluoromethyl, alkylsulphinyl, alkylsulphonyloxy, arylsulphonyloxy, acylamino or heterocyclyl.

When P in formula (A) is substituted the substituent(s) in turn may themselves be optionally substituted where appropriate with one or more of the aforementioned substituents.

As used herein the term "alkoxy" refers to a group having the formula AlkO— where Alk is alkyl as defined above. Typical alkoxy groups include, for example, methoxy, ethoxy, and t-butoxy.

The term "aryloxy" refers to a group having the formula ArO— where Ar is aryl as defined above. Typical aryloxy groups include, for example, phenoxy and naphthyloxy.

The term "acyl" refers to acyl groups derived from carboxylic acids having from 1 to 20 carbon atoms such as acetyl, propionyl, butyryl, valeryl, isovaleryl and hexanoyl.

The term "aroyl" refers to a group having the formula $$Ar-\underset{\underset{O}{\|}}{C}-$$

where Ar is an aryl group as defined above. Typical aroyl groups include, for example, benzoyl.

The terms "alkylthio", "alkylsulphinyl" and "alkylsulphonyloxy" refer to those groups having the formula AlkS—, AlkSO— and AlkSO$_2$—O— respectively where Alk is as defined above.

The terms "arylthio" and "arylsulphonyloxy" refer to those groups having the formula ArS— and Ar—SO$_2$—O— respectively where Ar is as defined above.

The term "amino" refers to a group of the formula $$-N\begin{matrix}Alk^1\\ \\Alk^2\end{matrix}$$

where Alk$^1$ and Alk$^2$ are the same or different and are hydrogen or a group Alk as defined above and thus includes primary, secondary and tertiary amino groups. Typical amino groups include, for example, NH$_2$, methylamino, ethylamino, dimethylamino and diethylamino.

"Halo" as used herein refers to iodo, bromo, chloro or fluoro groups.

The term "acylamino" as used herein refers to an amine group bearing on the nitrogen atom, an acyl group as herein defined.

Of the compounds of the general type represented by formula (A) the compounds of formula (IA) below are preferred for use in pharmaceutical formulations for administration as inhibitors of thromboxane synthetase.

Accordingly the present invention provides a pharmaceutical formulation which comprises an imidazole of formula (IA)

$$R-A-N\underset{=N}{\diagup\!\!\!\!\!\diagdown} \qquad (IA)$$

wherein
(i) A is a straight or branched alkylene group having 1, 2, 3 or 4 carbon atoms, or a straight or branched alkenylene group having 2, 3 or 4 carbon atoms, and R is a naphthyl, tetrahydronaphthyl, heterocyclyl (preferably with the proviso that the heterocyclyl group is not formed by an alkylenedioxy group of 1 to 4 carbon atoms e.g. a methylenedioxy group, attached to adjacent positions on a benzene ring attached to the group A), arylthio, arylalkylthio, aryloxy, arylalkyloxy, arylhydroxymethylene, arylcarbonyl, arylalkylcarbonyl, alkyloxy, alkylthio group or a cycloalkyl or cycloalkenyl group of from 4 to 9 carbon atoms substituted by a group other than a hydrocarbon group,
(ii) A is an —SO$_2$— group, and R is an aryl or heterocyclyl group, or
(iii) A is a chemical bond and R is a heterocyclyl group, or a pharmaceutically acceptable acid addition salt of such an imidazole, and a pharmaceutically acceptable carrier for the imidazole or salt thereof.

Preferably in the compounds of formula (IA) the group A is methylene (—CH$_2$—).

In the compounds of formula (IA) the various groups R are preferably substituted by one or more hydroxy, alkyloxy, halo or alkyl group(s), preferably by one or more hydroxy, methoxy, chloro, bromo or methyl group(s) where not excluded by definition of R.

Particularly preferred compounds for use in the pharmaceutical formulations are:
1-(1-naphthylmethyl)imidazole and its salts, and
1-(2-methyl-1-naphthylmethyl)imidazole and its salts.

Of the compounds of formula (IA) those of formula (I) are novel:

$$R-A-N\underset{=N}{\diagup\!\!\!\!\!\diagdown} \qquad (I)$$

wherein
(i) A is a straight or branched alkylene group having 1, 2, 3 or 4 carbon atoms or a straight or branched alkenylene group of 2, 3 or 4 carbon atoms, and R is selected from:
(a) a naphthyl group of formula wherein the two n's together are 0 or an integer of from 1 to 3, and the or each B, which, when the two n's together are greater than 1, may be the same or different, is halo, or alkyl or alkyloxy of from 1 to 3 carbon atoms,
(b) a tetrahydronaphthyl group,
(c) a heterocyclyl group, with the proviso that when the heterocyclyl group is 2-pyridyl, 1-methylbenzimidazol-2-yl, 2- or 3-indolyl, 1-piperidinyl, or 1-morpholinyl or, optionally, thienyl, the group A has 3 or 4 carbon atoms and, preferably, with a second proviso that the heterocyclyl group is not formed by an alkylenedioxy group of 1 to 4 carbon atoms, e.g. a methylenedioxy group, attached to adjacent positions on a benzene-ring attached to the group A;
(d) an arylhydroxymethylene group;
(e) an arylcarbonyl group;
(f) an arylalkylcarbonyl group;
(g) an alkyloxy group;
(h) an alkylthio group; or
(i) a cycloalkyl or cycloalkenyl group of from 4 to 9 carbon atoms substituted by a group other than a hydrocarbon group; or
(ii) A is an —SO$_2$— group, and R is an aryl or heterocyclyl group; or an acid addition salt of such an imidazole.

In these compounds of formula (I) the group A is preferably methylene

Preferably the group R in the compounds of formula (I) is, where possible, substituted by one or more hydroxy, alkyloxy, halo or alkyl group(s), preferably by one or more hydroxy, methoxy, chloro or bromo, or methyl group(s).

A particularly preferred class of compounds are those of formula (IB)

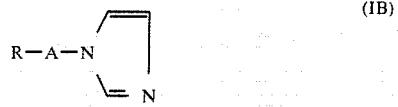
(IB)

wherein A is a straight or branched alkylene group having 1, 2, 3 or 4 carbon atoms or a straight or branched alkenylene group having 2, 3 or 4 carbon atoms, and R is a naphthyl group of formula

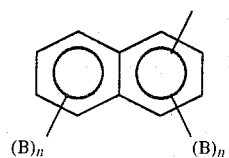

wherein the two n's together are O or an integer of from 1 to 3, and the or each B, which when the two n's together are greater than 1 may be the same or different, is halo, or alkyl or alkyloxy of from 1 to 3 carbon atoms, or an acid addition salt of such an imidazole.

Preferred compounds of formula (I) are:
1-(1-naphthylmethyl)imidazole and its salts, and
1-(2-methyl-1-naphthylmethyl)imidazole and its salts.

Known compounds of formula (IA) that may be used in the pharmaceutical formulations include 1-skatolylimidazole,
1-(2-pyridyl)imidazole,
1-(3-pyridyl)imidazole,
1-(4-pyridyl)imidazole,
1-(4-(2-hydroxymethyl)pyridyl)imidazole,
1-(2-(3-cyano)pyrimidyl)imidazole,
2-(imidazol-1-yl)-1-methylbenzimidazole
1-(2-hydroxynaphth-1-yl methyl)imidazole,
1(2-pyridylmethyl)imidazole,
1-[2-(2-pyridyl)ethyl]imidazole,
1-[2-(4-methyl-2-pyridyl)ethyl]imidazole,
1-[2-(4,6-dimethyl-2-pyridyl)ethyl]imidazole,
1-[2-(6-methyl-2-pyridyl)ethyl]imidazole,
1-(1-methylindol-2-ylmethyl)imidazole,
1-(1-piperidinylmethyl)imidazole,
1-(1-morpholinylmethyl)imidazole,
1-[2-(1-morpholinyl)ethyl]imidazole,
2-(imidazol-1-ylmethyl)-1-methylbenzimidazole,
and their pharmaceutically acceptable acid addition salts.

The skatolyl and 2-hydroxynaphthalene derivatives may be made by the method described by G. Decodts and M. Wakselman in Compt. Rend. C 266 (15) 1168-70 (1968). The 2-pyridylethyl compounds may be made by the method of E. Profft and W. Georgi, Ann. 643, 136-44, (1961). The 2-pyridylmethyl compound may be made by the method of R. J. Sundberg et al, J. Heterocycl. Chem. 14(7), 1279-81(1977). The benzimidazolyl compound may be prepared by the method of Kolodyazhnaya, S. N. et al, Khim.Geterotsikl.Soedin. 1970 (2) 238-44. The piperidinyl compound may be prepared by the method of Fred. B. Stocker et al, J. Org. Chem. 1970, 35(4), 883-7; the 1-morpholinylmethyl compound may also be made by the same method. The 1-morpholinylethyl compound is known from French Patent Specification No. 1486817.

In contrast to imidazole and 1-methyl-imidazole the compounds of formulae (I) and (IA) are more potent inhibitors of $TXA_2$ synthetase. Many of the compounds are also more selective in their action in not inhibiting other antiaggregatory-prostaglandin generating enzymes. The compounds of formulae (I) and (IA) also do not produce the side-effects found with imidazole upon in vivo administration. The compounds of formulae (I) and (IA) are further capable of inhibiting platelet aggregation in vivo and also are capable of disaggregating platelet clumps.

The compounds of formula (I) are suitable for use in the treatment or prophylaxis of angina pectoris. In some cases it is possible to prevent the onset of angina pectoris, for example when a patient with coronary artery disease is given cardiac pacing, which leads generally to an increase of $TXA_2$ in the blood, and which is associated with the onset of angina pectoris. Also, inhibition of $TXA_2$ formation prevents or delays the onset of shock, e.g. experimentally induced shock in laboratory animals.

Imidazoles of formulae (I) and (IA) and acid addition salts thereof may be made by any method known in the art for the synthesis of compounds of analogous structure. In general these methods preferably comprise (a) linking the imidazole ring to the remainder of the molecule; (b) converting a precursor molecule by elimination of a functional group from the imidazole or aromatic ring; or (c) formation of the desired compound from a corresponding pyrazole, imidazoline, or other unsaturated analogue.

A most convenient method of synthesis involves the reaction of imidazole (formula II) or a salt thereof with an agent of formula (III):

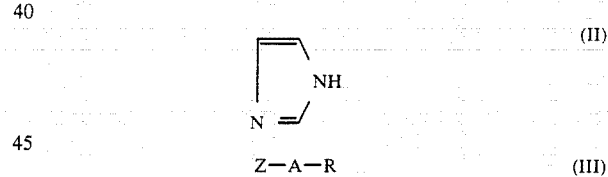

wherein R and A are as defined in formula (I) or (IA) and Z is a leaving group. This reaction is well established in the literature, and the leaving group may be chosen from variety of substituents but especially halo, preferably chloro or bromo, or from p-toluenesulphonyloxy, but other arylsulphonyloxy, alkanesulphonyloxy or arylalkylsulphonyloxy radicals may be used. The reaction is preferably performed in the presence of an acid acceptor, for example an alkali metal alkoxide, such as sodium methoxide or potassium tertiary butoxide in the presence of an alkanol. When Z is halo, the reaction may be carried out in the presence of a copper catalyst, eg. as in an Ullmann reaction, especially when A is a chemical bond. The leaving group Z may itself be formed in situ from the corresponding alkanol (Z=OH) by reaction with a hydrohalogenic acid (e.g. hydrochloric acid or a Lewis acid, such as aluminium chloride: see Japanese Patent Kokai No. 131577/77) and the resulting agent of formula (III) reacted directly with imidazole without prior isolation. Alternatively an alkanol (X=OH) or a derivative thereof (e.g. Z=R-A-O) may be reacted directly with imidazole (II) by heating in the presence of a dehydrating agent such as phosphoric acid, or a phosphate (see Japanese Patent Publication No. 51 105 060), sulphuric acid or sulphates (see Japanese Patent Publication No. 51 105 061).

Among precursor molecules which may be converted to a compound of formula (I) or (IA) or an acid addition salt thereof, are substituted imidazole derivatives of formula (IV), or addition salts thereof:

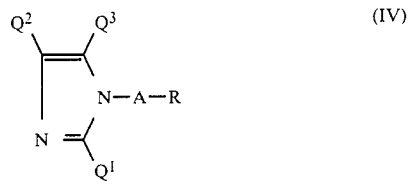

(IV)

wherein A and R are as defined in formula (I) or (IA) and $Q^1$, $Q^2$ and $Q^3$ are the same or different, at least one being a radical capable of removal by, for example, reduction or oxidation, the remaining radical or radicals being independently selected from hydrogen or a radical capable of removal in the same or another manner (e.g. a carboxyl group—see formula (VI)—removed by decarboxylation) with the proviso that when R is or includes aryl or aromatic heterocyclyl, removable groups like $Q^1$ etc. may be, or may also be, on aryl or heterocyclyl ring(s) in R in the starting material and removed from there. $Q^1$, $Q^2$ and $Q^3$ may be selected for example from thio (—SH), alkylthio (S-alkyl, wherein alkyl has from 1 to 4 carbon atoms) or halo preferably chloro or bromo. The reaction conditions are chosen according to the nature of the removable radicals such as $Q^1$, $Q^2$ and $Q^3$. Desulphurisation may be performed by oxidative or reductive procedures using, from example, nitric acid or Raney nickel; and reductive dehalogenation by the use of zinc and acetic acid or Raney nickel or other reagents known in the art or described in the literature.

Another class of examples include carboxyimidazoles or derivatives thereof of formula (VI):

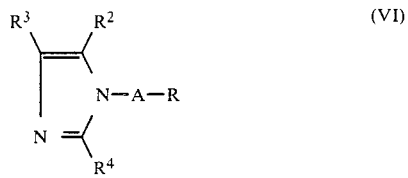

(VI)

wherein A and R are as defined for formula (I) or (IA) at least one of $R^1$, $R^2$ and $R^4$ is carboxyl or a derivative thereof (for example an ester such as an alkyl ester, an acid halide such as the chloride, or the nitrile) and the other is, or the others are independently, hydrogen or carboxyl or a derivative as described, (with the proviso that when R is, or includes, aryl or aromatic heterocyclyl the removable groups $R^1$, $R^2$ etc may be (or may also be) on the aryl or heterocyclyl ring(s) and removed from there) may be converted into the imidazoles of formula (I) or (IA) by any suitable decarboxylation conditions which may simply comprise heating the compounds with or without a catalyst, such as copper.

The imidazoles of formula (I) or (IA) may also be made from a compound of formula (VII):

(VII)

wherein

is 1-imidazoline, 1-imidazole or 1-pyrazole, $A^1$ is a straight or branched saturated or unsaturated acyclic hydrocarbon radical of 1 to 4 carbon atoms which may include a keto group, and R is as defined in formula (I) or (IA) provided that at least one of

$A^1$ and $R^3$ is other than 1-imidazole, a saturated or unsaturated hydrocarbon and R of the product of formula (I) or (IA).

Thus an imidazoline (VIII):

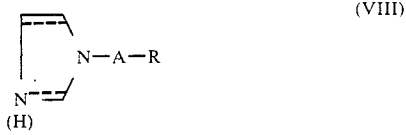

(VIII)

wherein one of ----- represents an extra bond and, A and R are as defined in formula (I) or (IA) may be dehydrogenated to the corresponding imidazole in the presence of a catalyst, for example by heating to 250° C. in the presence of palladium, nickel or platinum under pressure, or by heating with a dehydrogenating agent, such as selenium or copper oxide. 1-Pyrazole compounds (VII) may be treated with ultra-violet radiation, optionally under an inert atmosphere (e.g. argon) in for example 1,2-dimethoxyethane at room or elevated temperature (see for example "Ring Transformations of Heterocycles" edited van der Plas, Academic Press, 1973 at page 261). The unsaturated imidazoles of formula (I) or (IA) (in formula (VII), $A^1$ and/or unsaturated including aromatic) R may be reduced to the corresponding less saturated or completely saturated compounds (but not reducing the 1-imidazolyl nucleus) e.g. by hydrogenation with a noble metal catalyst, for example platinum or palladium in an alkanol.

A compound of, for example, formula (IX)

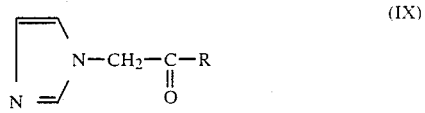

(IX)

where R is as defined in formula (I) or (IA), may be reduced at the keto group to a —CH$_2$— group for example by a Clemmensen reduction.

When R is aryl or aromatic heterocyclyl, alkyl groups (or other groups, eg keto groups) may be introduced into the aryl or heterocyclyl ring by a Friedel Crafts or similar Lewis-acid catalysed reaction for example of the type:

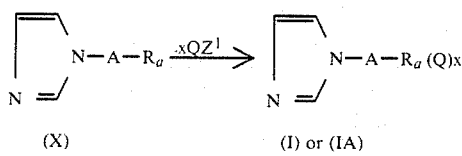

wherein A is as defined for formula (I) of (IA): $R_a$ is an aryl or aromatic heterocyclyl R (R being as defined for formula (I) or (IA)) x is an integer less than or equal to the number of unsubstituted positions in the aromatic ring(s) of $R_a$, Q is an alkyl or acyl group and $Z^1$ is a leaving group, e.g. halo, suitable for use in this type of reaction.

Compounds of formula (I) or (IA) may also be prepared by cyclising, preferably in the presence of an acid acceptor, a compound of formula

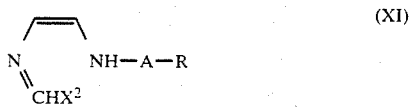

wherein A and R are as defined for formula (I) or (IA) and $X^2$ is a leaving group.

Compounds of formula (I) or (IA) may also be prepared by reacting compound of formula

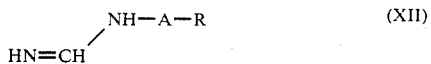

wherein A and R are as defined for formula (I) or (IA), with a compound of formula:

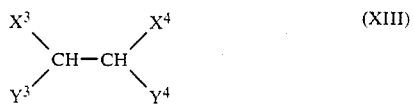

wherein either of $X^3$ and $Y^3$ is a leaving group such as halo or hydroxy and the other is hydrogen, or $X^3$ and $Y^3$ are both halo or, together with the CH group to which they are attached, form an aldehyde group or an acetal derivative thereof e.g. both $X^3$ and $Y^3$ are alkoxy; and $X^4$ and $Y^4$ are as defined for $X^3$ and $Y^3$, although they may be the same as or different from $X^3$ and $Y^3$.

An imine salt of for example formula:

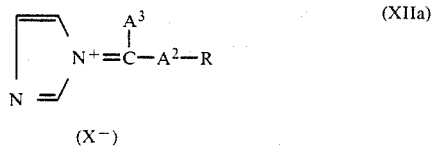

(wherein R is as defined for formula (I) or (IA), $X^-$ is an anion, $A^2$ is a chemical bond or a straight or branching, saturated or unsaturated acyclic hydrocarbon radical, which may include a keto group, $A^3$ is hydrogen or a saturated or unsaturated acyclic hydrocarbon radical, which may include a keto group, with the proviso that $A^2$ and $A^3$ together contain no more than 3 carbon atoms), may be reduced to the corresponding compound of formula (I) or (IA) by e.g. zinc and a mineral acid, e.g. hydrochloric acid.

When R in formula (I) or (IA) is substituted cycloalkyl or substituted cycloalkenyl, the substituents may be introduced by reaction of carbon to carbon double or triple bonds in an intermediate cycloalkenyl or cycloalkynyl compound with a suitable electrophilic reagent capable of adding across the double or triple bond(s) to provide the substituents in the cycloalkyl or cycloalkenyl group. For example a di-bromocycloalkyl R group can be made by brominating a compound in which R is a cycloalkenyl group with a solution of bromine in an organic solvent such as chloroform. A di-hydroxycycloalkyl R group may be prepared by oxidising a compound in which R is cycloalkenyl, for example with peracetic acid or with osmium tetroxide and hydrogen peroxide.

When R is heterocyclyl group to which the A group is attached by a nitrogen atom in the heterocyclic ring, the compound of formula (I) or (IA) may be prepared by a Mannich reaction reacting imidazole (II) with the parent heterocyclyl compound containing an —NH— group in the heterocyclyl ring and an aldehyde (to form the linking group A) which may have 1,2,3 or 4 carbon atoms. In this Mannich reaction the imidazole and heterocyclyl group will in the product be attached to the same carbon atom of A.

Preferably the reaction between the heterocyclyl compound and the aldehyde, preferably, formaldehyde, is carried out before the reaction with the imidazole, the reaction with the imidazole preferably being carried out in acidic solution.

The intermediates for use in the above described reactions may also be made by conventional methods known in the art. Thus the 1-pyrazole and 1-imidazoline intermediates (formula (VII)) may be prepared by alkylation of pyrazole and imidazoline in an analogous manner to that described above for preparation of the corresponding imidazoles. The intermediates of formula (III) may be made in known manner preferably by halogenation of the corresponding alcohols (formula (III), $Z = -OH$) where in such compounds R is substituted cycloalkenyl the alcohol is conveniently prepared by the Prins reaction from the substituted cycloalkene and paraformaldehyde (cf. *Bull. Chem. Soc.* Japan 46/48, 2512-5, 1973). Similarly when R is aryl and A is unsaturated with 3 or 4 carbon atoms the alcohol may be prepared from paraformaldehyde and the corresponding unsaturated-A compound with 2 or 3 carbon atoms. The substituted imidazole intermediates of formula (IV) may be made in known manner, for example see "Imidazole and its derivatives" Part I, Hd. K. Hoffman, Interscience Publishers, Inc. New York, 1973. For example the 2-thioimidazoles of formula (IV) may be made by cyclisation of an acetal of formula (XIV):

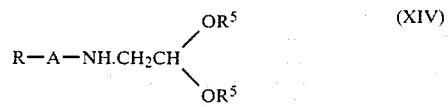

with thiocyanate, wherein $R^5$ is alkyl, aryl or arylalkyl.

The pharmaceutically acceptable acid addition salts of the compounds of formula (I) or (IA) may be prepared by any method known in the art. In particular they may be prepared by treating the parent imidazole with the appropriate acid. Examples of the addition salts of the compounds of formula (I) or (IA) include those salts derived from the following acids: oxalic, hydrochloric, hydrobromic, sulphuric, nitric, perchloric, fumaric, maleic, phosphoric, glycollic, lactic, salicylic, succinic, toluene-p-sulphonic, tartaric, acetic, citric, methanesulphonic, formic, benzoic, malonic, naphthalene-2-sulphonic and benzenesulphonic.

The imidazoles of formula (I) or (IA) may be used in conjunction with a phosphodiesterase inhibitor, which provides a further, synergistic increase in effect, as it acts against platelet aggregation by a different pathway.

Suitable (cyclic AMP) phosphodiesterase inhibitors for use in potentiating the anti-aggregatory effects of the active compounds include as such or as pharmaceutically acceptable salts:

(a) Xanthine derivatives such as:

Theophylline (3,7-dihydro-1,3-dimethyl-1$\underline{H}$-purine-2,6-dione), Caffeine (3,7-dihydro-1,3,7-trimethyl-1$\underline{H}$-purine-2,6-dione); and Aminophylline (adduct of Theophylline and 1,2-ethanediamine (2:1)).

Isoquinoline derivatives, for example: papaverine (1-[(3,4-dimethoxyphenyl)methyl]-6,7-dimethoxyisoquinoline);

(b) Derivatives of pyrimido (5,4-d)-pyrimidine, for example:

Dipyridamole (2,2′,2″,2‴-(4,8-dipiperidinopyrimido[5,4-d]pyrimidin-2,6-diyldinitrilo)-tetraethanol) and its salts;

(c) Derivatives of thieno[3,2-d]pyrimidine, for example:

N-[4-(4-morpholinyl)thieno[3,2-d]pyrimidin-2-yl]-1,2-ethanediamine.

(d) Derivatives of pyrazolo[3′,4′.2,3]pyrido[4,5-b]-[1,5]benzodiazepin-6-(3$\underline{H}$)one, for example: 3-Ethyl-7,12-dihydro-7,12dimethylpyrazolo-[4′,3′:3,0]pyrido[4,3-b]-[1,5]benzodiazepin-6-(3$\underline{H}$)-one;

(e) Derivatives of 1$\underline{H}$- or 2$\underline{H}$-pyrazolo[3,4-b]pyridine, for example:

4-(Butylamino)-1-ethyl-1$\underline{H}$-pyrazolo[3,4-b]-pyridine-5-carboxylic acid ethyl ester; and 2-Methyl-6-phenyl-4-(1-piperidinyl)-2$\underline{H}$-pyrazolo-[3,4-b]pyridine- (f) Derivatives of 5$\underline{H}$-furo-[3,4-e]pyrazolo-[3,4-b]pyridine-5-one, for example:

4-(Butylamino)-1-ethyl-1,7-dihydro-7-hydroxy-5$\underline{H}$-furo[3,4-c]pyrazolo[3,4-b]pyridine-5-one; and (g) Derivatives of 1-(2$\underline{H}$)-naphthalenone, for example:

2-(Dimethylamino)methyl-3,4-dihydro-7-methoxy-1(2$\underline{H}$)-naphthalenone or its salts e.g. its 1:1 hydrochloride.

The active compounds are particularly useful in the treatment and/or prophylaxis of thrombo-embolic disorders in mammals, including man. It is to be understood that the term "thrombo-embolic disorder" includes those disorders whose etiology is associated with platelet aggregation.

The active compounds are useful wherever it is desired to inhibit platelet aggregation and/or to reduce the adhesive character of platelets, and consequently to treat or prevent the formation of thrombi in mammals, including man. For example, the compounds are useful in the treatment and prevention of myocardial infarcts, cerebro-vascular thrombosis and ischaemic peripheral vascular disease; to treat and prevent post-operative thrombosis; and to promote patency of vascular grafts following surgery.

The active compounds are also useful as an addition to blood, blood products, blood substitutes, and other fluids which are used in artificial extracorporeal circulation and perfusion of isolated body portions, e.g., limbs and organs, whether attached to the original body, detached and being preserved or prepared for transplant, or attached to a new body. It may also be used in laboratory animals, e.g. cats, dogs, rabbits, monkeys and rats, for these purposes in order to develop new methods and techniques for organ and limb transplants.

The active compounds also exhibit some vasodilatory action on blood vessels and therefore have a utility as antihypertensives for the treatment of high blood pressure in mammals, including man.

The active compounds may also be used in the prevention, treatment or prophylaxis of angina pectoris, and in the prevention or delay of the onset of shock.

The amount of active compound required for therapeutic or prophylactic effect will vary with the route of administration, and the nature of the condition under treatment. In general a suitable dose for a mammal, including man, of active compound will lie in the range of 0.1 to 300 mg per kg body weight, particularly from 0.5 to 10 mg per kg body weight, for example 2 mg per kg. A suitable single oral dose for an adult human lies within the range of 50 to 600 mg, preferably 100 to 300 mg, for example 150 mg given say three times a day.

While it is possible for an active compound to be administered as the raw chemical, it is preferable to present it as a pharmaceutical formulation. The formulations, both for veterinary and for human medical use, of the present invention comprise an active compound as above defined, together with one or more acceptable carriers therefor and optionally other therapeutic ingredients. The carrier(s) must be 'acceptable' in the sense of being compatible with the other ingredients of the formulation and not deleterious to the recipient thereof. Unit doses of a formulation may contain between 60 mg and 1.5 g of an active compound.

The formulations include those suitable for oral, rectal, vaginal or parenteral (including subcutaneous, intramuscular and intravenous) administration. Preferred formulations include tablets, capsules and injectable suspensions or solutions.

The formulations may conveniently be presented in unit dosage form and may be prepared by any of the methods well known in the art of pharmacy. All methods include the step of bringing into association the active compound (in the form of the base or a pharmaceutically acceptable acid addition salt) with the carrier which constitutes one or more accessary ingredients. In general the formulations are prepared by uniformly and intimately bringing into association the active compound with liquid carrier(s) or finely divided solid carrier(s) or both, and then, if necessary, shaping the product into the desired formulation.

It will be appreciated from the foregoing that the present invention provides the following features:

(a) Novel 1-substituted imidazoles of formula (I) and acid addition salts thereof.

(b) Methods of preparing imidazoles of formula (I) and acid addition salts thereof.

(c) Pharmaceutical formulations containing the imidazoles of formula I(A) or a pharmaceutically acceptable acid addition salt thereof and a pharmaceutically acceptable carrier.

(d) Method of preparing the pharmaceutical formulations containing the imidazoles of formula I(A) or a pharmaceutically acceptable acid addition salt thereof.

(e) A method for the treatment or prophylaxis of a thrombo-embolic disorder in a mammal or mammalian tissue, including man or human tissue, comprising administering an active compound.

(f) A method of prevention, treatment or prophylaxis of angina pectoris in a mammal, including man, which comprises administering to the mammal an effective amount of an imidazole of formula (IA) or a pharmaceutical acceptable acid addition salt thereof.

(g) A method of preventing or delaying the onset of shock in a mammal, including man, which comprises administering to the mammal an effective amount of an imidazole of formula (IA) or a pharmaceutically acceptable salt thereof.

The following Examples are provided by way of an illustration of the present invention and should in no way be construed as constituting a limitation thereof. All temperatures are given in degrees Celsius.

EXAMPLE 1

(a) Preparation of 2-(2-Bromoethyl)naphthalene

A solution of phosphorus tribromide (3.52 g, 0.013 mol) in chloroform (6.25 ml) was added dropwise at $-10°$ to a stirred solution of 2-naphthalene-ethanol (4.3 g, 0.025 mol) in chloroform (20 ml), containing dry pyridine (0.13 ml, 0.0016 mol). Following the addition, the mixture was stirred at $-10°$ for 2 h, and was then stood at ambient temperature overnight. Next day, the reaction mixture was poured into water (62.5 ml) and the organic layer was separated. The aqueous solution was then extracted with chloroform ($3 \times 6.25$ ml), and the organic layer and chloroform extracts were combined and washed with sodium hydroxide solution (62.5 ml, 2M), and with water (62.5 ml). The chloroform solution was dried ($MgSO_4$), and the chloroform was then evaporated under reduced pressure to afford 2-(2-bromoethyl)naphthalene which was used without further purification.

(b) Preparation of 1-[2-(2-Naphthyl)ethyl]imidazole

A mixture of imidazole (1.02 g, 0.015 mol), 2-(2-bromoethyl)naphthalene (3.53 g, 0.015 mol) and potassium tert-butoxide (1.68 g, 0.015 mol) in dry butan-1-ol (100 ml) was stirred and heated under reflux for 29 h.

After cooling, the reaction mixture was filtered, and the filtrate was concentrated to afford a light brown oil. The oil was suspended in hydrochloric acid (45 ml, 2M), and the acid solution was washed with ether (45 ml). The acid solution was then basified with sodium hydroxide solution (10M) and the product was then extracted with chloroform. The chloroform extracts were combined and dried ($MgSO_4$), when removal of the chloroform under reduced pressure afforded an oil which was purified using a silica gel column and by elution with chloroform/methanol (9:1). The product fractions were pooled and concentrated to afford the product as a brown solid. Recrystallisation of the solid from ethyl acetate/light petroleum afforded a white solid, m.p. $98°-99°$.

EXAMPLE 2

(a) Preparation of 1-(2-Bromoethyl)naphthalene

A mixture of hydrobromic acid (50 ml, 46% w/v) and 1-(2-hydroxyethyl)naphthalene (10.0 g, 0.058 mol) was stirred and heated under reflux for 4 h. After cooling, the reaction mixture was diluted with water (150 ml), and the resulting precipitate was extracted with ether ($3 \times 150$ ml). The ether extracts were combined and dried ($MgSO_4$), when the ether was evaporated under reduced pressure, to afford 1-(2-bromoethyl)naphthalene which was used without further purification.

(b) Preparation of 1-[2-(1-Naphthyl)ethyl]imidazole

A mixture of imidazole (3.9 g, 0.057 mol), 1-(2-bromoethyl)naphthalene (13.4 g, 0.057 mol) and potassium tert-butoxide (6.4 g, 0.057 mol) in dry butan-1-ol (100 ml) was stirred and heated under reflux for 26 h.

After cooling, the reaction mixture was filtered, and the filtrate was evaporated under reduced pressure to afford an oil. The oil was dissolved in hydrochloric acid (150 ml, 2M), and the acid solution was washed with ether (150 ml). The acid solution was then basified with sodium hydroxide solution (10M) and the basic solution was then extracted with chloroform ($3 \times 100$ ml). The chloroform extracts were combined and dried ($MgSO_4$). Removal of the chloroform under reduced pressure afforded an oil which was purified using a silica gel column and by elution with chloroform/methanol. The product fractions were combined and concentrated, to give an oil which was distilled, yielding 1-[2-(1-naphthyl)ethyl]imidazole as a viscous yellow oil, b.p. $150°/0.01$ mm Hg.

EXAMPLE 3

Preparation of 1-(1-Naphthylmethyl)imidazole

1-Bromomethylnaphthalene (5.6 g, 0.0253 mol) was added dropwise to a stirred boiling solution of imidazole (1.72 g, 0.0253 mol) and sodium bicarbonate (2.13 g, 0.0253 mol) in dry methanol (40 ml). Following the addition, the reaction mixture was stirred and boiled for 6 h.

After cooling, the reaction mixture was concentrated under reduced pressure, and the residue was suspended in water (70 ml). The aqueous mixture was extracted with chloroform ($3 \times 70$ ml), and the chloroform extracts were combined and dried. The residue was chromatographed using a silica gel column and by elution with chloroform/methanol (9:1). The product fractions were combined, concentrated, and the residue was distilled, to afford 1-(1-naphthylmethyl)imidazole, b.p. $150°-156°/0.1$ mm Hg.

EXAMPLE 4

Preparation of 1-(2-Methyl-1-naphthylmethyl)imidazole

1-Chloromethyl-2-methylnaphthalene (9.55 g, 0.05 mol) was added dropwise to a solution of imidazole (3.4 g, 0.05 mol) and potassium tert-butoxide (5.6 g, 0.05 mol) in dry butan-1-ol. Following the addition, the reaction mixture was stirred and heated under reflux for 3 h.

After cooling, the reaction mixture was filtered, and the filtrate was concentrated under reduced pressure to afford a brown oil. The oil was dissolved in hydrochloric acid (150 ml, 2M), and this mixture was washed with ether ($1 \times 150$ ml). The aqueous solution was then basified with sodium hydroxide solution (10M) and the resulting oil was extracted with chloroform ($3 \times 100$ ml). The chloroform extracts were combined, dried ($MgSO_4$), and then concentrated to afford a brown oil. A portion of the oil (5 g) was purified using a silica gel column and by elution with chloroform/methanol (9:1). The product fractions were pooled and concentrated to afford a solid, which was recrystallised from ethyl acetate/petroleum ether (b.p. $40°-60°$), giving 1-(2-methyl-1-naphthylmethyl)imidazole as a fawn solid, m.p. $98°-98.5°$.

EXAMPLE 5

Preparation of 1-(5,5-Dimethyl-1,3-dioxan-2-ylmethyl)imidazole

A mixture of imidazole (6.8 g, 0.1 mol), potassium tert-butoxide (11.2 g, 0.1 mol) and 2-chloromethyl-5,5-dimethyl-1,3-dioxane (16.5 g, 0.1 mol) in dry butan-1-ol (150 ml) was stirred and heated under reflux for 16 h.

After cooling, the reaction mixture was filtered, and the filtrate was concentrated under reduced pressure to afford a brown oil. The oil was dissolved in hydrochloric acid (100 ml, 2M), and the acid solution was washed with ether (1×100 ml). The acid solution was then basified with sodium hydroxide solution (10M) and the product was extracted with chloroform (2×100 ml). The chloroform extracts were combined, dried (MgSO$_4$), and then concentrated to afford an oil. The oil was purified using a silica gel column, and by elution with chloroform/methanol (9:1). The product fractions were pooled, concentrated, and the residue was distilled, to afford 1-(5,5-dimethyl-1,3-dioxan-2-ylmethyl)imidazole, b.p. 98°–104°/0.15 mm Hg.

EXAMPLE 6

Preparation of 1,1'-Tetramethylenedi-imidazole

A mixture of imidazole (13.6 g, 0.2 mol) and sodium butoxide (prepared from sodium (4.6 g, 0.2 mol) and dry butan-1-ol (100 ml)) was stirred and heated to 70°, when 1,4-dibromobutane (43.2 g, 0.2 mol) was added dropwise at such a rate that the internal temperature did not exceed 75°. Following the addition, the reaction mixture was then stirred and heated at 70° in a sealed vessel for 20 h.

After cooling, the reaction mixture was filtered, and the filtrate was concentrated under reduced pressure to afford an oil. Distillation of the residual oil gave the product as a colourless oil, b.p. 183°–185°/0.1 mmHg, which solidified on standing. Recrystallization of the solid from ethyl acetate/petroleum ether (b.p. 40°–60°) gave 1,1'-tetramethylenedi-imidazole, m.p. 84°–86°.

EXAMPLE 7

Preparation of 1-(2-Tetrahydrofuranylmethyl)imidazole

A solution of 2-chloromethyltetrahydrofuran (1.205 g, 0.01 mol), imidazole (0.68 g, 0.01 mol) and potassium tert-butoxide (1.12 g, 0.01 mol) in dry butan-1-ol (8 ml) was stirred and heated under reflux for 16 h.

After cooling, the reaction mixture was concentrated under reduced pressure, and the residue was extracted with chloroform (4×25 ml). The chloroform extracts were concentrated to afford a yellow oil which was purified using a silica gel column, and by elution with chloroform/methanol (9:1). The product fractions were pooled, concentrated, and the residue was distilled, to afford 1-(2-tetrahydrofuranylmethyl)imidazole, b.p. 86°–88°/0.05 mm Hg.

EXAMPLE 8

Preparation of 1-(3-Pyridylmethyl)imidazole

A solution of 3-chloromethylpyridine hydrochloride (11.5 g, 0.07 mol) in methanol (30 ml) was added dropwise to a stirred, boiling mixture of imidazole (4.8 g, 0.07 mol) and sodium bicarbonate (11.8 g, 0.14 mol) in methanol (100 ml). Following the addition, the mixture was stirred and boiled for 6 h.

After cooling, the reaction mixture was filtered, and the filtrate was evaporated to dryness. The residue was dissolved in hydrochloric acid (100 ml), and the acid solution was washed with ether (2×100 ml). The acid solution was then basified with sodium hydroxide solution (10M), and basic mixture was extracted with chloroform (3×100 ml). The chloroform extracts were combined, dried (MgSO$_4$), and the chloroform was then removed under reduced pressure to yield a black oil which was purified using a silica gel column and by elution with chloroform/methanol (9:1). The product fractions were pooled, concentrated under reduced pressure, and the residue was distilled to afford 1-(3-pyridylmethyl)imidazole, b.p. 140°–142°/0.25 mm Hg.

EXAMPLE 9

(a) Preparation of 2-Chloromethyl-1,4-Benzodioxan

A mixture of thionyl chloride (36.0 g, 0.3 mol) and 2-hydroxymethyl-1,4-benzodioxan (25.0 g, 0.15 mol) was stirred and heated under reflux for 0.75 h. The reaction mixture was concentrated under reduced pressure, and the residue was distilled, to afford 2-chloromethyl-1,4-benzodioxan, b.p. 140°–146°/22 mm Hg.

(g) Preparation of 1-(1,4-Benzodioxan-2-ylmethyl)imidazole

A mixture of imidazole (5.35 g, 0.0078 mol), 2-chloromethyl-1,4-benzodioxan (14.5 g, 0.078 mol) and potassium tert-butoxide (8.82 g, 0.078 mol) in dry butan-1-ol (100 ml) was stirred and heated under reflux for 30 h.

After cooling, the reaction mixture was filtered, and the filtrate was concentrated under reduced pressure to afford a brown oil. The oil was dissolved in hydrochloric acid (150 ml), and the acid solution was washed with ether (1×150 ml). The aqueous layer was then basified with sodium hydroxide solution (10M), and the basic solution was extracted with chloroform (3×100 ml). The chloroform extracts were then combined and dried (MgSO$_4$), when removal of the chloroform under reduced pressure afforded an oil which was purified using a silica gel column and by elution with chloroform/methanol (9:1). The product fractions were pooled and concentrated to give an oil which was distilled to afford 1-(1,4-benzodioxan-2-ylmethyl)imidazole, b.p. 148°/0.13 mm Hg.

EXAMPLE 10

Preparation of 1-(2-Quinolylmethyl)imidazole

A solution of 2-Chloromethylquinoline hydrochloride (10.7 g, 0.05 mol) in methanol (50 ml) was added dropwise to a stirred, boiling solution of potassium tert-butoxide (11.2 g, 0.1 mol) and imidazole (3.4 g, 0.05 mol) in dry butan-1-ol. Following the addition, the reaction mixture was stirred and heated under reflux for 5 h. After removal of the butan-1-ol under reduced pressure, the resulting orange oil was dissolved in hydrochloric acid (150 ml, 2M), and the acid solution was washed with ether (3×100 ml). The acid solution was then basified with sodium hydroxide solution (10 m), and the basic solution was then extracted with chloroform (3×100 ml). The chloroform solutions were combined, dried (MgSO$_4$), and the chloroform was then evaporated to afford an oil which was purified using a silica gel column and by elution with chloroform/methanol (9:1). The product fractions were pooled, concentrated, and the resulting solid was recrystallized from aqueous ethanol, to afford, 1-(2-quinolylmethyl)imidazole as buff crystals, m.p. 106°–108°.

EXAMPLE 11

Preparation of 1-(Benzenesulphonyl)imidazole

A mixture of imidazole (27.2 g, 0.4 mol), and benzenesulphonyl chloride (35.3 g, 0.2 mol) in dry tetrahydrofuran (200 ml) was stirred at ambient temperature for 1 h, when the resulting precipitate was removed by filtration. The filtrate was evaporated under reduced pressure and the resulting solid was recrystallised from benzene/petroleum ether (b.p. 40°–60°), to afford 1-(benzenesulphonyl)imidazole, m.p. 82°–83°.

EXAMPLE 12

Preparation of 1-(2-Hydroxy-2-phenylethyl)imidazole

A solution of imidazole (47.0 g, 0.69 mol) in 'super-dry' ethanol (175 ml) containing dry pyridine (3.0 ml) was stirred and heated to 75° when styrene oxide (80.0 g, 0.67 mol) was added dropwise at such a rate that the temperature of the reaction mixture was maintained at 80°–85°. Following the addition, the reaction mixture was stirred until the internal temperature had fallen to 50°. Isopropyl ether (300 ml) was then added to the reaction mixture, and the resulting mixture was poured into iced-water (1,000 ml). Separation of the resulting solid by filtration afforded the product which was washed with acetone ($1 \times 500$ ml) and with ether ($2 \times 300$ ml), to give 1-(2-hydroxy-2-phenylethyl)imidazole, m.p. 149°–151°.

EXAMPLE 13

Preparation of 1-(Benzoylmethyl)imidazole

A solution of α-bromoacetophenone (45.0 g, 0.226 mol) in methanol (150 ml) was added dropwise to a stirred solution of imidazole (13.6 g, 0.2 mol) and sodium hydroxide solution (25 ml, 10M) in methanol (100 ml) at 75°. Following the addition, the reaction mixture was stirred at ambient temperature for 20 h.

The reaction mixture was then evaporated to dryness and the residue was suspended in water (150 ml). The aqueous mixture was extracted with chloroform ($3 \times 100$ ml), and the chloroform extracts were washed with sodium bicarbonate solution (100 ml) and were then dried (MgSO$_4$). The chloroform was then removed under reduced pressure to give a residue which was purified using a column of silica gel and by elution with chloroform/methanol (9:1). The product fractions were pooled and concentrated, to afford a solid which was recrystallised from toluene, to give 1-(benzoyl methyl)imidazole as a white solid, m.p. 121°–122°.

EXAMPLE 14

Preparation of 1-(2-Ethylthioethyl)imidazole

A mixture of bromoethyl ethyl sulphide (16.9 g, 0.1 mol), potassium tert-butoxide (11.2 g, 0.1 mol) and imidazole (6.8 g, 0.1 mol) was stirred and heated under reflux for 11 h.

After cooling, the reaction mixture was filtered, and the filtrate was concentrated under reduced pressure to give a brown oil. The oil was suspended in hydrochloric acid (150 ml) and the acid solution was washed with ether ($2 \times 100$ ml). The acid solution was then basified with sodium hydroxide solution (10M), and the basic solution was extracted with chloroform ($3 \times 150$ ml). The chloroform extracts were combined and dried (MgSO$_4$), when evaporation of the chloroform afforded a brown oil which was purified using a silica gel column, and by elution with chloroform/methanol (9:1).

The product fractions were pooled and concentrated to afford 1-(2-ethylthioethyl)imidazole, b.p. 141°–143°/15 mm Hg.

EXAMPLE 15

Preparation of 1-(3-Oxapentyl)imidazole

2-Chloroethyl ethyl ether (25.0 ml, 0.225 mol) was added dropwise to a stirred, boiling solution of imidazole (13.6 g, 0.2 mol) in ethanolic sodium ethoxide (prepared from sodium (4.6 g, 0.2 mol) in dry ethanol (100 ml)). Following the addition, the reaction mixture was stirred and boiled for 6 h.

After cooling, the reaction mixture was concentrated under reduced pressure, and the residue was suspended in water (150 ml). The aqueous suspension was extracted with chloroform ($3 \times 50$ ml), and the combined chloroform extracts were dried (MgSO$_4$) and then concentrated under reduced pressure to give an oil. The oil was purified using a silica gel column and by elution with chloroform/methanol (9:1). The product fractions were combined and concentrated to afford an oil, which was distilled, to afford 1-(3-oxapentyl)imidazole, b.p. 140°/14 mm Hg.

EXAMPLE 16

Preparation of 1-(2-Phenoxyethyl)imidazole

2-Phenoxyethyl bromide (22.62 g, 0.1 mol) was added dropwise to a stirred, boiling solution of imidazole (6.8 g, 0.1 mol) in ethanolic sodium ethoxide (Prepared from sodium (2.75 g, 0.12 mol) and dry ethanol (100 ml)). Following the addition, the reaction mixture was stirred and boiled for 4 h.

After cooling, the reaction mixture was filtered and the filtrate was concentrated under reduced pressure. The residue was suspended in water (100 ml), and the aqueous suspension was extracted with chloroform ($3 \times 100$ ml). The combined chloroform extracts were dried (MgSO$_4$), and the chloroform was then removed under reduced pressure to afford an oil. The oil was purified using a silica gel column and by elution with chloroform/methanol (9:1). The product fractions were pooled, concentrated, and the resulting white solid was recrystallised from ethyl acetate/light petroleum, to afford 1-(2-phenoxyethyl)imidazole, m.p. 88°.

EXAMPLE 17

Preparation of 1-(3-Phenyl-1-oxapropyl)imidazole

Chloromethyl benzyl ether (32.3 g, 0.2 mol) was added dropwise to a stirred, boiling solution of imidazole (13.6 g, 0.2 ml) and ethanolic sodium ethoxide (prepared from sodium (4.6 g, 0.2 mol) in dry ethanol (150 ml)). Following the addition, the reaction mixture was stirred and heated under reflux for 8 h.

After cooling, the reaction mixture was filtered, and the filtrate was concentrated under reduced pressure to afford an oil which was purified using a silica gel column and by elution with chloroform/methanol (9:1). The product fractions were pooled, concentrated, and the residual oil was distilled, to afford 1-(3-phenyl-2-oxapropyl)imidazole, b.p. 122°–124°/0.15 mm Hg.

EXAMPLE 18

Preparation of 1-(Phenylthiomethyl)imidazole

A mixture of chloromethyl phenyl sulphide (2.0 g, 0.0126 mol), potassium carbonate (1.8 g, 0.013 mol) and imidazole (0.94 g, 0.014 mol) in dry acetone (20 ml) was stirred and heated under reflux for 23 h.

After cooling, the reaction mixture was filtered, and the filtrate was concentrated under reduced pressure to give a brown residue. The residue was dissolved in ether (200 ml), and the ether solution was washed with water (5×50 ml). The ether solution was then extracted with hydrochloric acid (2×50 ml, 1M), and the acid extracts were then basified with sodium hydroxide solution. The resulting oil was extracted with ether (3×100 ml), and the ether extracts were combined and dried (MgSO$_4$). Evaporation of the ether under reduced pressure gave an oil which was purified using a silica gel column and by elution with chloroform/methanol (9:1). The product fractions were pooled and concentrated, to afford an oil which was distilled, giving 1-(phenylthiomethyl)imidazole, b.p. 102°–103°/0.025 mm Hg.

EXAMPLE 19

Preparation of 1-(3,4-Dibromocyclohexylmethyl)imidazole

A solution of bromine (2 ml) in chloroform (25 ml) was added dropwise to a stirred solution of 1-(cyclohex-3-enylmethyl)imidazole (2.5 g, 0.015 mol) in chloroform at 25°. Following the addition, chloroform (50 ml) was added to the reaction mixture, when a heavy red oil separated. The chloroform layer was separated, dried (MgSO$_4$), and was then concentrated under reduced pressure to afford 1-(3,4-dibromocyclohexylmethyl)imidazole.

Attempted distillation of the above oil resulted in substantial decomposition.

The product was pure as examined by thin layer chromatography (using chloroform/methanol (9:1) as eluent), by nuclear magnetic resonance spectroscopy, and by high resolution mass spectrometry:

| m/e (Calculated) | 319.9524 | Based on $^{79}$Br. |
|---|---|---|
| m/e (Observed) | 319.9522 | |

EXAMPLE 20

Preparation of 1-(2-Phthalimidoethyl)imidazole

N-(2-Bromoethyl)phthalimide (28.0 g, 0.11 mol) was added to a stirred mixture of sodium bicarbonate (84 g, 0.1 mol) and imidazole (6.8 g. 0.1 mol) in dry methanol (100 ml). Following the addition, the reaction mixture was stirred and heated under reflux for 13 h.

The reaction mixture was then concentrated under reduced pressure, and the residue was suspended in water (100 ml). The product was extracted with chloroform (3×100 ml), and the chloroform solutions were combined and dired (MgSO$_4$). The chloroform solution was concentrated under reduced pressure, and the resulting oil was purified using a silica gel column, and by elution with chloroform/methanol (9:1). The product fractions were combined and concentrated, giving a solid which was recrystallised from ethanol, to afford 1-(2-phthalimidoethyl)imidazole, m.p. 151°–153°.

EXAMPLE 21

Preparation of 1-(5-Chlorothien-2-ylmethyl)imidazole

5-Chloro-2-chloromethylthiophene (11.0 g, 0.066 mol) was added dropwise to a stirred mixture of imidazole (4.0 g, 0.058 mol) and sodium bicarbonate (5.4 g, 0.064 mol) in dry methanol (50 ml). Following the addition the reaction mixture was stirred and heated under reflux for 20 h.

The reaction mixture was then concentrated under reduced pressure, and the residue was dissolved in hydrochloric acid (150 ml, 2M). The acidic solution was washed with ether (1×150 ml), and the acid solution was then basified with sodium hydroxide solution (10M). The basic solution was extracted with chloroform (3×100 ml), and the combined chloroform extracts were washed with water (1×100 ml) and then dried (Na$_2$SO$_4$). The chloroform solution was concentrated under reduced pressure and the resulting oil was purified using a silica gel column and by elution with chloroform/methanol (9:1). The product fractions were pooled and concentrated, to afford 1-(5-chlorothien-2-ylmethyl)-imidazole as a pale yellow oil.

NMR (CDCl$_3$) δ 5.15 (2H, s, CH$_2$), 6.75 (2H, s, thienyl), 6.95 (1H, s, imidazole), 7.05 (1H, s, imidazole), and 7.5 (1H, s, imidazole).

EXAMPLE 22

Preparation of a Mixture of 5-Chloromethyl-1,2,3,4-tetrahydronaphthalene and 6-Chloromethyl-1,2,3,4-tetrahydronaphthalene This mixture of compounds was prepared according to the methods of R. H. Wightman et al., J. Org. Chem., 1978, 43, 2167 and R. T. Arnold and R. Barnes, J. Amer. Chem. Soc., 1943, 65, 2393.

Preparation of a 50:50 Mixture of: 1-(1,2,3,4-Tetrahydronaphth-5-ylmethyl)imidazole and 1-(1,2,3,4-Tetrahydronaphth-6-ylmethyl)imidazole A solution of potassium tert-butoxide (4.48 g, 0.04 mol) and imidazole (2,72 g, 0.04 mol) in dry butan-1-ol (100 ml) was stirred and heated under reflux when a 50:50 mixture of 5-chloromethyl-1,2,3,4-tetrahydronaphthalene and 6-chloromethyl-1,2,3,4-tetrahydronaphthalene (7.25 g, 0.04 mol) was added dropwise. Following the addition, the reaction mixture was stirred and heated under reflux for 4 h.

After cooling, the reaction mixture was filtered, and the filtrate was concentrated under reduced pressure. The residue was dissolved in hydrochloric acid (150 ml, 2M), and the acid solution was washed with ether (2×50 ml). The acid solution was then basified with sodium hydroxide solution (10M). The basic solution was then extracted with chloroform (3×50 ml), and the chloroform extracts were combined and dried. Evaporation of the chloroform afforded a yellow oil which was purified using a silica gel column and by elution with chloroform/methanol (9:1). The product fractions were pooled and concentrated to afford an oil which was distilled, yielding a 50:50 mixture of 1-(1,2,3,4-tetrahydronaphth-5-ylmethyl)imidazole and 1-(1,2,3,4-tetrahydronaphth-6-ylmethyl)imidazole, b.p. 128°–132°/0.01 mm Hg.

NMR (CDCl$_3$) δ 1.6–1.9 (4H, m), 2.4–2.9 (4H, m), 4.95 (s, CH$_2$), 5.0 (s, CH$_2$), 4.95 and 5.0 together 2H. 6.65–7.05 (5H, m, Ar and imidazole) and 7.4 (1H, d, imidazole).

The signals (δ 4.95 and 5.0) due to the methylene groups linking the imidazole ring to the rest of the molecule were of equal intensity.

EXAMPLE 23

Preparation of 1-(2-pyridylmethyl)imidazole

A solution of 2-chloromethylpyridine hydrochloride (16.4 g, 0.1 mol) in ethanol (50 ml) was added dropwise to a stirred, boiling solution of potassium tert-butoxide (22.4 g, 0.2 mol) and imidazole (6.8 g, 0.1 mol) in dry butan-1-ol (100 ml). Following the addition, the reaction mixture was stirred and heated under reflux for 5 h. After removal of the solvents under reduced pressure, the resulting oil was dissolved in hydrochloric acid (150 ml, 2M), and the acid solution was washed with ether (100 ml). The acid solution was then basified with sodium hydroxide solution (10M), and the basic solution was extracted with chloroform (3×100 ml). The chloroform solutions were combined, dried (MgSO$_4$), and the chloroform was then removed under reduced pressure. The residue was purified by using a silica-gel column and by elution with chloroform/methanol (9:1). The resulting solid was recrystallised from ethanol/light petroleum affording 1-(2-pyridylmethyl)imidazole as white cubes m.p. 79°–80°.

EXAMPLE 24

Preparation of Salts of 1-(Naphthylmethyl)imidazole (a) Hydrogen Fumarate

A solution of fumaric acid (0.21 g) in hot ethanol (10 ml) was added to a solution of 1-(1-naphthylmethyl)imidazole (0.4 g) in ethanol (5 ml). After boiling for 10 minutes, the solution was evaporated under reduced pressure to afford a white solid. Recrystallisation of the solid from ethanol afforded 1-(1-naphthylmethyl)imidazole, hydrogen fumarate, m.p. 159°–161° C.

(b) Hydrogen Succinate

A solution of succinic acid (0.22 g) in hot ethanol (10 ml) was added to a solution of 1-(1-naphthylmethyl)imidazole (0.4 g) in ethanol (5 ml). After boiling for 10 minutes, the solution was evaporated under reduced pressure to afford a white solid. Recrystallisation of the solid from ethyl acetate afforded 1-(1-naphthylmethyl)imidazole hydrogen succinate, m.p. 121°–123° C.

(c) Hydrogen Oxalate

A solution of oxalic acid dihydrate (0.25 g) in hot ethanol (10 ml) was added to a solution of 1-(1-naphthylmethylimidazole (0.43 g) in ethanol (5 ml). The solution was boiled for 10 minutes, when the ethanol was removed under reduced pressure to afford a white solid. Recrystallisation of the solid from ethanol afforded 1-(1-naphthylmethyl)imidazole hydrogen oxalate, m.p. 139°–141° C.

EXAMPLE 25

Preparation of 1-(2-Chloro-4,5-methylenedioxybenzyl)imidazole

A solution of 2-chloro-4,5-methylenedioxybenzyl chloride hydrochloride (10.0 g, 0.041 mol) in methanol (30 ml) was added dropwise to a stirred, boiling solution of potassium tert-butoxide (9.2 g, 0.082 mol) and imidazole (2.7 g, 0.038 mol) in dry butan-1-ol. Following the addition, the reaction mixture was stirred and heated under reflux for 6 h.

After cooling, the reaction mixture was filtered, and the filtrate was concentrated under reduced pressure to afford an orange oil. The oil was dissolved in hydrochloric acid (100 ml, 2M), and the acid solution was washed with ether (2×100 ml). The acid solution was then basified with sodium hydroxide soluton (10M), and the basic mixture was then extracted with chloroform (3×150 ml). The chloroform extracts were combined, dried (MgSO$_4$), and then concentrated to give an oil which was purified using a silica gel column, and by elution with chloroform/methanol (9:1). The product fractions were pooled and concentrated, to give an oil which crystallised on standing. Recrystallisation of the solid from benzene/light petroleum gave 1-(2-chloro-4,5-methylenedioxybenzyl)imidazole as buff crystals, m.p. 99°–102°.

EXAMPLE 26

By the method of Example 1(b) the following compounds were made:

(a) 1-(2-naphthylmethyl)imidazole,
(b) 1-(1-(4-methylnaphthyl)methyl)imidazole,
(c) 1-(1-(2-methoxy naphthyl)methyl)imidazole,
(d) 1-(1-methylpiperidin-3-ylmethyl)imidazole,
(e) 1-(6-uracilylmethyl)imidazole,
(f) 1-(3-(1-piperidinyl)propyl)imidazole,
(g) 1-(2-(1-pyrrolidinyl)ethyl)imidazole,
(h) 1-(2-(2-piperidinyl)ethyl)imidazole,
(i) 1-(3-(3-pyridyl)propyl)imidazole,
(j) 1-(2-furanylmethyl)imidazole

EXAMPLE 27

By the method of Example 18 the following compounds were made:

(a) 1(Benzylthiomethyl)imidazole and
(b) 1-(2-Phenylthio)ethyl)imidazole.

EXAMPLE 28

By the method of Example 19 the following compounds were made, in each case bromine being replaced by the reagent indicated (a) 1-(cis-3,4-dihydroxycyclohexylmethyl)imidazole using osmium tetroxide and hydrogen peroxide.
(b) 1-(trans-3,4-dihydroxycyclohexylmethyl)imidazole using peracetic acid.

BIOLOGICAL RESULTS EXAMPLE

Horse platelets were prepared from whole horse blood by differential centrifugation. Approximately $10^6$ platelets were homogenised in 1 ml 100mM Tris buffer pH 7.4. Various concentrations of active compound were added and the reaction sets incubated for 5 minutes at ambient temperature. To each tube was added 20nM of arachidonic acid containing $10^6$ disintegrations per minute (DPM) of labelled arachidonic acid and the tubes incubated for 3 minutes at 37° C. in a shaking water bath. After incubation the radioactive products were extracted from the acidified aqueous phase with ethyl acetate and after concentration resolved by thin layer chromatography on silica gel with chloroform/methanol/acetic acid/water (90:8:1:0.8) as a developing solvent. The amount of thromboxane produced was measured by scraping off the radioactive zone corresponding to thromboxane B$_2$ and estimating the radioactivity in a liquid scintillation counter.

The concentration of active compound to reduce the enzyme activity by 50% (ED$_{50}$) was established. The results are shown in Table A.

The selectivity of the active compounds was measured in a similar manner to that described above and the amount of PGE, PGF and PGD produced was determined. The greater the selectivity, the more of the anti-aggregating prostaglandins are produced.

The FD$_{50}$ and Selectivity results are shown in Table A in which 0 indicates no selectivity; + low selectivity; ++ medium selectivity; +++ high selectivity; and ND not determined.

TABLE A

| Compound (Reference compound) | ED$_{50}$ μg/ml | Selectivity |
| --- | --- | --- |
| (Imidazole) | ≧500 | 0 to + |
| (1-Methylimidazole) | ≧200 | ++ |
| 1-[2-(1-Naphthyl)ethyl]imidazole | ~5 | ++ |
| 1-(1-Naphthylmethyl)imidazole | 2–5 | ++(+) |
| 1-(2-tetrahydrofuranylmethyl)imidazole | ≧100 | +++ |
| 1-(1,4 benzodioxan-2-ylmethyl)imidazole | 5–7 | + |
| 1-(2-hydroxy-2-phenylethyl)imidazole | 25 | ND |
| 1-(2-Ethylthioethyl)imidazole | 30 | ND |
| 1-(2-methyl-1-naphthylmethyl)imidazole | <5 | ++(+) |

FORMULATION EXAMPLES

EXAMPLE A-TABLET FORMULATION

Imidazole of formula (I) as a solid or a solid salt thereof: 150 mg
Starch: 25 mg
Polyvinylpyrrolidone: 2 mg
Magnesium stearate: 3 mg The imidazole or salt is ground to a fine powder, blended with the starch and then the mixture granulated with an aqueous solution of the polyvinylpyrrolidone. The granules are sieved 1000μ, dried, sieved again and the magnesium stearate added. The mixture is then compressed into tablets.

In this manner, tablets of 1-(1-naphthylmethyl)imidazole (as a salt) and of 1-(2-methyl-1-naphthylmethyl)imidazole (as a salt) were prepared.

EXAMPLE B-TABLET FORMULATION

Tablets (150 mg) of the imidazoles or salts described in the preceding Example are prepared as in the same manner from the following ingredients:

The Imidazole Compound (as a solid or as a solid salt): 150 mg
Lactose: 100 mg
Starch: 30 mg
Polyvinylpyrrolidone: 2 mg
Magnesium stearate: 3 mg In the preparation, the lactose is blended with the starch.

EXAMPLE C-TABLET FORMULATION

Tablets (100 mg) of the imidazoles or salts of Example A are prepared in the same manner from the following ingredients:

The Imidazole Compound (as a solid or as a solid salt): 100 mg
Sodium starch glycollate: 10 mg
Polyvinylpyrrolidone: 2 mg
Magnesium stearate: 3 mg

EXAMPLE D-TABLET FORMULATION

Tablets (150 mg) of the imidazoles or salts of Example A are prepared in the same manner from the following ingredients, except that the starch, pregelled starch and imidazole compound are all blended together prior to granulation:

The Imidazole Compound (as a solid or as a solid salt): 150 mg
Starch: 25 mg
Pregelled starch: 5 mg
Magnesium stearate: 3 mg

EXAMPLE E-INJECTABLE FORMULATION

Imidazole compound (or salt) of formula (IA): 15.0 g
Lactic Acid B.P.: q.s. to pH 3.0
Water for Injections B.P.: to 100.0 ml Suspend the compound in ¾ of the available quantity of water. Add sufficient lactic acid to dissolve the compound and to reduce the pH to 3.0. Dilute to volume with Water for Injections.

Sterilise the solution by passage through a membrane filter, pore size 0.22 μm.

Distribute the solution using aseptic precautions into sterilised ampoules, 1 ml per ampoule. Seal by fusion of the glass.

Each 1 ml ampoule supplies 150 mg of the imidazole compound e.g. 1-(1-naphthylmethyl)imidazole or 1-(2-methyl-1-naphthylmethyl)imidazole.

EXAMPLE F-INJECTABLE FORMULATION

Imidazole compound or salt of formula (IA): 15.0 g
Citric Acid B.P.: q.s. to pH 3.0
Chlorocresol: 0.1 g
Water for Injections to: 100.0 ml Suspend the compound in ½ the final volume of Water for Injections. Add sufficient citric acid as a 10% solution in Water for Injections to dissolve the compound and reduce the pH to 3.0. Dilute to volume with Water for Injections.

Sterilise the solution by passage through a membrane filter, pore size 0.22 μm.

Distribute the solution with aseptic precautions into sterilised vials, 25 ml per vial. Stopper with sterile rubber closures and seal with an aluminium cap.

Each 1 ml of solution provides 150 mg of the compound e.g. 1-(1-naphthylmethyl)imidazole or 1-(2-methyl-1-naphthylmethyl)imidazole.

EXAMPLE G-INJECTABLE FORMULATION

In the same manner described in the preceding two Formulation examples, injectable formulations of 1-(2-hydroxy-2-phenylethyl)imidazole salts were prepared.

I claim:

1. A pharmaceutical formulation for use in inhibiting TXA$_2$ synthetase which comprises an effective TXA$_2$ synthetase inhibition amount of an imidazole of formula (IA)

wherein
(i) A is a straight or branched alkylene group having 1, 2, 3 or 4 carbon atoms or a straight or branched alkenylene group having 2, 3 or 4 carbon atoms, and R is a
naphthyl,
tetrahydronaphthyl,
heterocyclyl,
arylthio,
arylalkylthio,
aryloxy,
arylalkyloxy,
alkyloxy,
(ii) A is an —SO$_2$— group, and R is an aryl or a heterocyclyl group, (iii) A is a chemical bond and R is a heterocyclyl group, or a pharmaceutically acceptable acid addition salt of such an imidazole, and a pharmaceutically acceptable carrier for the imidazole or salt thereof.

2. A formulation according to claim 1 wherein in the imidazole
(i) A is a straight or branched alkylene group having 1, 2, 3 or 4 carbon atoms or a straight or branched alkenylene group of 2, 3 or 4 carbon atoms, and R is a
  naphthyl,
  tetrahydronaphthyl,
  heterocyclyl, or
  a cycloalkyl or cycloalkenyl group of from 4 to 9 carbon atoms substituted by a group other than a hydrocarbon group,
(ii) A is an —SO$_2$— group, and R is an aryl or an aromatic heterocyclyl group,
(iii) A is a chemical bond and R is a heterocyclyl group, or a pharmaceutically acceptable acid addition salt of such an imidazole.

3. A formulation according to claim 1 wherein, in the imidazole or salt thereof, the group R is substituted by one or more hydroxy, alkyloxy, halo or alkyl group.

4. A formulation according to claim 1 wherein, in the imidazole or salt thereof, the group R is substituted by one or more hydroxy, methoxy, chloro, bromo or methyl group.

5. A formulation according to claim 1 in which A in formula (IA) is methylene.

6. A formulation according to claim 1 wherein the imidazole is 1-(1-naphthylmethyl)imidazole or an acid addition salt thereof.

7. A formulation according to claim 1 wherein the imidazole is 1-(2-methyl-1-naphthylmethyl)imidazole or an acid addition salt thereof.

8. A formulation according to claim 1 in the form of a parenterally acceptable injectable solution or suspension.

9. A formulation according to claim 1 which is orally ingestible.

10. A formulation according to claim 9 in the form of a tablet or capsule.

11. A formulation according to claim 10 wherein the imidazole is present as such or as salt in an amount of from 50 to 600 mg.

12. A formulation according to claim 11 wherein the amount is 150 mg.

13. A pharmaceutical composition for use in medicine inhibiting TXA$_2$ synethetase which comprises a medicinally effective TXA$_2$ synethetase inhibiting amount of 1-(1-naphthylmethyl)imidazole or a pharmaceutically acceptable salt thereof together with a pharmaceutically acceptable carrier therefore.

14. A pharmaceutical composition for use in medicine, inhibiting TXA$_2$ synethetase which comprises a medicinally effective TXA$_2$ synthetase inhibiting amount of 1-2-methyl-1-naphthylmethyl)imidazole or a pharmaceutically acceptable salt thereof together with a pharmaceutically acceptable carrier therefore.

15. A formulation of claim 1 wherein the imidazole is a 1-substituted imidazole of formula (I)

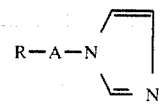

wherein
(i) A is a straight or branched alkylene group having 1, 2, 3 or 4 carbon atoms or a straight or branched alkenylene group of 2, 3 or 4 carbon atoms and R is selected from:
(a) a naphthyl group of formula

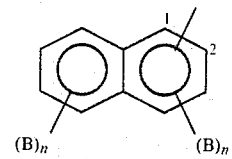

wherein the two n's together are 0 an integer of from 1 to 3, and the or each B, which when the two n's together are greater than 1 may be the same or different, is halo, or alkyl or alkyloxy of from 1 to 3 carbon atoms;
(b) a tetrahydronaphthyl group;
(c) a heterocyclyl group, with the proviso that when the heterocyclyl group is 2-pyridyl, 1-methylbenzimidazol-2-yl, or 2- or 3-indolyl, 1-piperidinyl, or 1-morpholinyl, the group A has 3 or 4 carbon atoms, or
(d) an alkyloxy group;
(e) an alkylthio group; or
(ii) A is an —SO—$_2$ group, and R is an aryl group or a heterocyclyl group, or a pharmaceutically acceptable acid addition salt of such imidazole.

16. A formulation of claim 1 wherein the imidazole is
(i) A is a straight or branched alkylene group having 1, 2, 3 or 4 carbon atoms or a straight or branched alkylene group of 2, 3 or 4 carbon atoms and R is selected from:
(a) a naphthyl group of formula

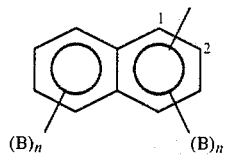

wherein the two n's together are 0 or an integer of from 1 to 3, and the or each B, which when the two n's together are greater than 1 may be the same or different, is halo, or alkyl or alkyloxy of from 1 to 3 carbon atoms:
(b) a tetrahydronaphthyl group;
(c) a heterocyclyl group, with the proviso that when the heterocyclyl group is 2-pyridyl, 1-methylbenzimidazol-2-yl, 2- or 3-indolyl, 1-piperidinyl, or 1-morpholinyl, the group A has 3 or 4 carbon atoms, or
(ii) A is an —SO$_2$— group, and R is an aryl group or a heterocyclyl group; or a pharmaceutically acceptable acid addition salt of such an imidazole.

17. A formulation of claim 15 wherein the imidazole in the group R is substituted by one or more hydroxy, alkyloxy, halo or alkyl group.

* * * * *